(12) United States Patent
Rizoiu

(10) Patent No.: US 8,479,745 B2
(45) Date of Patent: Jul. 9, 2013

(54) METHODS AND DEVICES FOR TREATING PRESBYOPIA

(75) Inventor: Ioana M. Rizoiu, San Clemente, CA (US)

(73) Assignee: Biolase, Inc., Irvine, CA (US)

( * ) Notice: Subject to any disclaimer, the term of this patent is extended or adjusted under 35 U.S.C. 154(b) by 866 days.

(21) Appl. No.: 12/540,579

(22) Filed: Aug. 13, 2009

(65) Prior Publication Data

US 2010/0042082 A1    Feb. 18, 2010

Related U.S. Application Data

(63) Continuation-in-part of application No. 11/413,590, filed on Apr. 26, 2006, now Pat. No. 7,665,467.

(60) Provisional application No. 61/088,719, filed on Aug. 13, 2008.

(51) Int. Cl.
  *A61B 19/00*    (2006.01)

(52) U.S. Cl.
  USPC .............................................. 128/898; 606/4

(58) Field of Classification Search
  USPC .......... 606/3–6, 10, 166; 607/88, 89; 128/898
  See application file for complete search history.

(56) References Cited

U.S. PATENT DOCUMENTS

| 4,559,942 | A | * | 12/1985 | Eisenberg | 606/6 |
| 4,911,711 | A | | 3/1990 | Telfair et al. | |
| 6,241,721 | B1 | * | 6/2001 | Cozean et al. | 606/6 |
| 6,263,879 | B1 | | 7/2001 | Lin | |
| 6,706,036 | B2 | | 3/2004 | Lai | |
| 6,824,540 | B1 | | 11/2004 | Lin | |
| 7,146,983 | B1 | | 12/2006 | Hohla et al. | |
| 7,785,321 | B2 | * | 8/2010 | Baerveldt et al. | 606/6 |
| 8,315,280 | B2 | | 11/2012 | Zimare et al. | |
| 2003/0139737 | A1 | | 7/2003 | Lin | |
| 2003/0220630 | A1 | | 11/2003 | Lin et al. | |
| 2004/0006332 | A1 | | 1/2004 | Black | |
| 2004/0078009 | A1 | | 4/2004 | Lin | |
| 2006/0271025 | A1 | | 11/2006 | Jones et al. | |
| 2007/0123844 | A1 | | 5/2007 | Henry | |
| 2009/0207874 | A1 | | 8/2009 | Zimare et al. | |

FOREIGN PATENT DOCUMENTS

| JP | 3-44534 | 7/1991 |
| JP | 2009-534139 | 9/2009 |
| WO | 9201430 A1 | 2/1992 |
| WO | 02094129 A2 | 11/2002 |
| WO | 2005034730 A2 | 4/2005 |
| WO | 2005096766 A2 | 10/2005 |

OTHER PUBLICATIONS

Supplementary European Search Report, EP 08799256 (PCT/US2008/075476), mailed Dec. 30, 2010.
International Search Report, Application No. PCT/US2009/053684, Oct. 1, 2009.
First Office Action (with English translation) dated Nov. 27, 2012 issued in corresponding/related Japanese Patent Application No. 2011-523161 based on PCT/US2009/053684 filed Aug. 13, 2009, and U.S. Appl. No. 61/088,719, filed Aug. 13, 2008.

* cited by examiner

*Primary Examiner* — Ahmed Farah
(74) *Attorney, Agent, or Firm* — Jones Day

(57) ABSTRACT

Architectures and techniques for treating conditions of the eye, such as presbyopia, utilize sources of treatment energy, such as electromagnetic energy emitting devices, to implement non-corneal manipulations. According to these devices and methods, the sources of treatment energy are activated to direct energy onto parts of the eye, such as the conjunctiva and sclera, to treat presbyopia. The treatments can affect at least one property of the eye and enhance an accommodation of the eye.

11 Claims, No Drawings

METHODS AND DEVICES FOR TREATING PRESBYOPIA

CROSS-REFERENCE TO RELATED APPLICATIONS

This application claims the benefit of U.S. Provisional Application No. 61/088,719, filed Aug. 13, 2008 and entitled METHODS AND DEVICES FOR TREATING PRESBYOPIA, the entire contents of which are hereby incorporated by reference. This application is a continuation-in-part of U.S. application Ser. No. 11/413,590, filed Apr. 26, 2006 now U.S. Pat. No. 7,665,467 and entitled METHODS FOR TREATING EYE CONDITIONS, the entire contents of which are hereby incorporated by reference. This application is related to U.S. application Ser. No. 11/475,719, filed Jun. 26, 2006 and entitled VISUAL FEEDBACK IMPLEMENTS FOR ELECTROMAGNETIC ENERGY OUTPUT DEVICES, the entire contents of which are hereby incorporated by reference.

BACKGROUND OF THE INVENTION

1. Field of the Invention

The present invention relates generally to medical treatments and, more particularly, to methods and apparatus for treating eye disorders such as presbyopia using energies including infrared laser.

2. Description of Related Art

Two common ophthalmologic conditions relating to focusing disorders are known as myopia and hyperopia. Myopia, or nearsightedness, relates to an eyesight refractive abnormality whereby distant objects appear blurred as a result of rays of light entering the eye being brought to focus in front of the retina. Hyperopia, or farsightedness, on the other hand, relates to an eyesight refractive abnormality whereby near objects appear blurred or fuzzy as a result of light rays being brought to focus behind the retina.

One variation of hyperopia is presbyopia, which typically is associated with a person's lack of capacity to focus at near distances and which tends to develop and progress with age. Regarding this progression, presbyopia is thought to advance as the eye progressively loses its ability to accommodate or focus sharply for near vision with increasing age of the person. Accordingly, the condition of presbyopia generally signifies a universal decrease in the amplitude of accommodation of the affected person.

Myopia and hyperopia can be treated surgically using techniques including corneal interventions, such as reshaping a surface curvature of the cornea located inside of the limbus area, and non-corneal manipulations, such as altering properties of the sclera (which is located outside of the limbus area), ciliary muscle, zonules, or lens. An example of the former treatment can comprise ablating the surface of the cornea itself to form a "multifocal" arrangement (e.g., distance vision in one eye and reading vision in another eye according to a treatment plan referred to as monovision) facilitating viewing by a patient of both near and far objects, and an example of the latter treatment can comprise introducing kerfs into portions of the sclera to thereby increase accommodation. Non-corneal interventions typically comprise temporarily removing or pulling-back the patient's conjunctiva, using forceps and scissors and/or one or more of scalpels, cautery, plasma, and laser methods, followed by the actual non-corneal manipulations (e.g., forming kerfs in the sclera). After completing the kerfs, the conjunctiva is then typically sutured back into position.

SUMMARY OF THE INVENTION

Devices and methods of the present invention for treating conditions of the eye, such as presbyopia, utilize sources of treatment energy, such as electromagnetic energy emitting devices, to implement non-corneal manipulations. According to the architectures and techniques of the present invention, the sources of treatment energy can be activated to direct energy onto parts of the eye, such as the conjunctiva and sclera, to treat presbyopia, wherein the energy affects at least one property of the eye and results in an enhancement in an accommodation of the eye.

The source of treatment energy can comprise a source of electromagnetic energy, such as a laser. In certain implementations, the laser is an Erbium based, pulsed laser which emits optical energy into the sclera of the eye. Introduction of the treatment energy into the sclera can increase or facilitate an increase in accommodation of the eye, thereby mitigating the effects of presbyopia.

While the apparatus and method has or will be described for the sake of grammatical fluidity with functional explanations, it is to be expressly understood that the claims, unless expressly formulated under 35 U.S.C. 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. 112 are to be accorded full statutory equivalents under 35 U.S.C. 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

DETAILED DESCRIPTION OF THE INVENTION

Reference will now be made in detail to the presently preferred embodiments of the invention. Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by any appended additional disclosure (e.g., in claims format). It is to be understood and appreciated that the process steps and structures described or incorporated by reference herein do not cover a complete process flow for the implementations described herein. The present invention may be practiced in conjunction with various medical devices that are conventionally used in the art, and only so much of the commonly practiced method steps are included herein as are necessary to provide an understanding of the present invention.

Any feature or combination of features described herein are included within the scope of the present invention provided that the features included in any such combination are not mutually inconsistent as will be apparent from the context, this specification, and the knowledge of one of ordinary skill in the art.

As used herein, "accommodation" refers to the ability to change focus from distant objects to near objects, which ability tends to diminish with age.

As used herein, "choroid" refers to the highly vascular layer of the eye beneath the sclera.

As used herein, "ciliary muscle" refers to a muscular ring of tissue located beneath the sclera and attached to the lens via zonules.

As used herein, "conjunctiva" refers to the thin, transparent tissue covering the outside of the sclera.

As used herein, "cornea" refers to the clear central front tissue of the eye which can be considered to be a key component of the focusing system.

As used herein, "cornea epithelium" refers to the outermost skin or layer of the cornea.

As used herein, "limbus" refers to the boundary where the cornea meets the sclera.

As used herein, "retina" refers to the light-sensitive layer of tissue that lines the back of the eyeball and sends visual impulses through the optic nerve to the brain.

As used herein, "sclera" refers to the outer supporting structure, or "the white" of the eye.

As used herein, "vitreous body" refers to the clear colorless transparent jelly that fills the eyeball posterior to the lens and that is enclosed by a delicate hyaloid membrane.

As used herein, "zonules" refers to a circular assembly of radially directed collagenous fibers that are attached at their inner ends to the lens and at their outer ends to the ciliary muscle.

An inability of the eye to focus sharply on nearby objects, called "presbyopia," is associated with advancing age and typically entails a decrease in accommodation. Introduction of treatment energy (e.g., laser ablation), according to any of the implementations described herein, may increase or facilitate an increase in accommodation, thereby mitigating effects of presbyopia. In typical embodiments, introduction of treatment energy to the sclera tissue can increase the accommodation of the ciliary body to thereby allow the presbyopic patient to see both near and far.

In accordance with various aspects of the present invention, an accommodation can be augmented via introduction of a plurality of "tissue treatments," meaning apertures (e.g., in the form of spots) or pits formed (e.g., via ablation), or tissue areas otherwise contacted with treatment energy to visibly or non-visibly affect the tissue areas, in one or more of, for example, the cornea, limbus, conjunctiva, sclera, ciliary muscle, lens, and/or zonules. The tissue treatments may be formed by directing treatment energy from an external location toward the eye and/or may be formed by way of introducing an endoscopic device into an intraocular vicinity of the eye to thereby deliver treatment energy. The delivered treatment energy may facilitate formation of tissue treatments as described herein.

According to an aspect of the present invention, tissue treatments can be introduced into the sclera and/or ciliary muscle. In exemplary implementations, each of the tissue treatments comprises a shape, which may resemble a dot, spot, a short dash, or other object such as an elongated arc or a line. For instance, a maximum length dimension of a tissue treatment can range from about 0.01 mm to about 1 mm, a maximum width dimension can range from about 0.01 mm to about 1 mm, and a maximum depth dimension can range from about 0.01 mm up to about 5 mm (or, alternatively, up to about 1.0 mm). In certain embodiments, tissue treatments may be formed to have maximum diameters of about 1 µm to about 100 µm, and in particular implementations having maximum diameters of about 20 µm to about 50 µm. Tissue treatments may be implemented using lasers having wavelengths ranging, for example, from about 0.15 µm to about 3.2 µm. Exemplary laser beam spot sizes can range from about 0.001 mm up to about 1.0 mm (or, alternatively, up to about 2.0 mm), and exemplary laser energy per pulse values can range from about 0.1 mJ to about 50 mJ depending on, for example, the pulse duration and the laser beam spot size. Typical pulse laser widths may range from about 100 nanoseconds to about 1000 microseconds. The areas to be treated can be pre-traced with a vascular laser or even the long pulse Er,Cr:YSGG, or long pulse Er:YAG, to minimize any bleeding. A fiber optic tip may be used to focus electromagnetic (e.g., optical) energy onto, for example, the conjunctiva and/or sclera in order to form tissue treatments to depths of, for example, about 60% to about 99% of the sclera thickness (i.e., about 500 µm to 700 µm) and, in exemplary embodiments, depths between about 90% and 99% of the sclera thickness.

The treatment energy can have a focal point, which is on or in the sclera. A profile of the treatment energy can have one or more of a conical and a "V" shape. A characteristic or measurable parameter of the treatment energy can drop by about 1 to about 20 percent for each 1 percent drop in depth within the sclera.

One or more of the tissue treatments described herein may be introduced with parts or substantially all of the conjunctiva altered (e.g., removed, reconfigured or repositioned such as by separating and/or shifting the conjunctiva, relative to the sclera) before or during introduction of the one or more of the tissue treatments, in any order or sequence of steps. Thus, with any of the implementations described herein, parts of the conjunctiva may, in certain embodiments, be manipulated while other parts are left in a naturally-occurring orientation over the sclera. In other implementations, parts of the conjunctiva above portions of the sclera receiving tissue treatments may be manipulated and/or other parts of the conjunctiva above portions of the sclera receiving tissue treatments may be left in a naturally-occurring orientation over the sclera. Furthermore, with any of the implementations described herein, substantially all of the conjunctiva may be reconfigured or repositioned (e.g., shifted) relative to, for example, the sclera.

In certain embodiments, fluids, including water, sterile water or conditioned fluids, such as described in U.S. Pat. Nos. 5,785,521 and 6,350,123, the contents of which are incorporated herein by reference, may be added to ensure or aid in the cosmetic appeal of the treated tissue and/or to assist with healing time or other properties. For example, fluid (e.g., sterile water) may be applied by way of a small air mister (e.g., from a local or remotely-disposed canister or dropper) affixed, for example, to a device (e.g., an applicator device or output tip), between or, preferably, during application of treatment energies, to thereby attenuate or eliminate charring and/or wash away blood.

As another example, fluid (e.g., sterile water) may be applied by way of a small air mister or sprayer line affixed, for example, to a treatment energy (e.g., laser) device (e.g., handpiece) at or for any of the above-noted times or purposes. The line may comprise, for example, tubing (e.g., clip-on and/or silicone based tubing) secured to an outside or built into the device and a fluid dispensing input disposed on the device. The fluid-dispensing input may be activated, for example, to facilitate manual or powered dispensation of fluid. Manual dispensation may be implemented by way of, for example, a line leading to or integrally formed with a detachable container (e.g., pod) that can be squeezed by a user to dispense fluid (e.g., sterile water pre-packaged into a single-use, disposable pod), and powered dispensation may be implemented by way of a toggle button to initiate a powered output of fluid at, for example, a relatively low flow rate and pressure. An atomized distribution of fluid (e.g., sterile water) particles may be automatically applied to the target tissue during application of treatment energies, for example. In other examples, a drop of the fluid (e.g., sterile water) may be applied before or during application of treatment energies. In still further embodiments, treatment energies and fluid (e.g., sterile water) may be combined to facilitate electromagnetically induced mechanical cutting, as described in the preceding two patents, to enhance cutting attributes. Suction may be applied to any of the foregoing implementations, as well, for removing fluids, debris and/or liquids. For any embodiments employing suction for any purpose described herein, such as to secure a structure to a surface of the eye, specialized surfaces (e.g., relatively nonporous surfaces to facilitate suctional gripping and securement of the structure to the eye) and/or surface treatments (e.g., viscasil®) can be employed.

Tissue treatments in the conjunctiva may be closed using techniques known in the art such as sutures, surgical tacks, screws or staples, and/or applinator-style attachments including adhesives. An exemplary implementation can comprise a surgeon selecting a minimum amount of anesthesia needed to keep the patient comfortable, with the anesthesia comprising at least one of the following local anesthetics: 1% Tetracaine applied in a circular ring pledget around the ciliary body for five minutes; local subtenon's injection with 2% Lidocaine applied one quadrant at a time; and topical 2% Xylocaine gel applied 20-30 minutes prior to surgery. Topical 1% Proparacaine can be applied 5 minutes before the procedure and periodically during the procedure as deemed appropriate by the surgeon according to the patient's pain response. Topical 1% Tetracaine or 2% Lidocaine can also be used. A peribulbar injection comprising a 50/50 mixture of 2% Lidocaine with 0.75% Marcaine can be administered according to the clinical judgment of the investigator if the patient does not obtain effective anesthesia by any of the above methods. One drop of a topical antibiotic (Vigamox, Ciloxan or Zymar) and one drop of a topical non-steroidal anti-inflammatory (Acular LS or Voltaren) can also be applied. The patient can be prepared according to typical protocols for refractive surgery, with a lid speculum being inserted followed by placement of a cornea protector over the cornea.

Tissue treatments (e.g., incisions) can then be generated, wherein scleral tissue is ablated to about 95% of a total thickness (e.g., approximately 500-550 µm) of the sclera. The incisions can be generated using an Er,Cr:YSGG laser having a frequency of 30 Hz, a wavelength of 2.78 µm, and a spot size of 600 µm. The surgeon can watch for the characteristic dark blue hue of choroid as an endpoint during each ablation process. Subsequently, each of the peritomy sites can be closed with bipolar forceps, sutures or Tisseal glue, followed by placement of 1 drop NSAID and 1 drop antibiotic thereto. An eye patch or patches may be used only if needed, and the patient can be instructed to use his or her eyes for normal near and far vision immediately following surgery.

An exemplary implementation of a treatment energy (e.g., laser) device (e.g., handpiece) can comprise an Er,Cr:YSGG laser with a 600 µm quartz or sapphire (contact) tip operated at 1.25 W and 2.78 µm. For non-contact mode, the tip may be positioned approximately 0.5 to 3 mm from the surface. For contact mode procedures, the tip can be placed against tissue and moved along the tissue path applying only light pressure. Ophthalmic soft tissue surgical procedures, including incision, excision, vaporization and coagulation of ocular tissue and tissue surrounding the eye and orbit can be implemented with a treatment energy device known as the Oculase MD, manufactured by Biolase Technology, Inc. of Irvine, Calif. The incision and excision of skin is required in many cosmetic and functional peri-ocular procedures. Oculoplasty, including surgery (e.g., reconstructive surgery) of the eyelid or eyebrow, eyelid injuries, and lid retraction, to improve function, comfort and appearance, as well as blepharoplasty, etc., are all indications that can be implemented with the Oculase MD for precise incision and/or removal of skin with only superficial coagulation and little to no extensive thermal modifications.

The Er,Cr:YSGG Oculase MD laser has a distinct capability of precisely cutting and removing skin while producing only a minimal thermal effect into tissue adjacent to the cut (~40 µm) for surgical procedures (e.g. incision, excision and coagulation) related to peri-ocular cosmetic or functional indications. Oculase MD parameters for skin incision can be: P=0.25-1 W, f=20 Hz, $E_{pulse}$=10-50 mJ/pulse, tip type=OT4 or OZ4, A=7-11% (from a pressurized air supply line, e.g., of an Oculase MD) and W=1-3% (from a pressurized water supply line, e.g., of an Oculase MD). The incision is performed with the tip in contact mode positioned at approximately 70-90 degrees to the surface. Fiber tips such as the OZ4 and OT4 transfer a narrow beam of energy to the target providing for a very thin skin incision. By applying just slight pressure at the point of contact and with slow movement of the fiber tip along the tissue path the incision produced is fine and precise. The excision of skin may be started with an outline of the area that needs to be removed, using an OT4 or OZ4 tip at a setting such as: P=0.25-0.5 W, pulse frequency of 20 Hz, $E_{pulse}$=10-25 mJ/pulse, A=7-11% (from a pressurized air supply line, e.g., of an Oculase MD) and W=1-3% (from a pressurized water supply line, e.g., of an Oculase MD). In contact mode it is quick and effective to prepare the initial outline. A forceps may be used to lift one side of the skin to allow the fiber tip access for tissue excision. Separation of tissue is easily performed by undermining the tissue using a side to side motion with the tip almost parallel to the surface.

Laser tissue coagulation may be applied at any time to control bleeding at the site. The settings for this procedure can be: P=0.5-0.75 W, pulse frequency of 20 Hz, $E_{pulse}$=10-25 mJ/pulse, tip type=OG6 (4 or 6 mm length), noncontact mode or application. With the tip in a defocused mode at about 2 mm off the surface the area where there is an open bleeding wound can be quickly scanned. Areas with small bleeding vessels may require momentary application of the tip in contact to the tissue site to produce a deeper coagulation zone.

Removal of Soft Tissue Lesions

The Er,Cr:YSGG laser may also be used to remove peri-ocular soft tissue lesions such as skin tags, papilomas, keratosis, and cysts, wherein for example the chalazion can be drained to remove other such benign lesions. For superficial skin lesions such as tags and keratosis the best modality to excise such is to lift the lesion with a forceps and use the laser in contact mode to cut the tissue growth at the base. Settings for such procedures can be P=0.25-1W, f=20 Hz, $E_{pulse}$=10-50 mJ/pulse, tip type=OT4 or OZ4 tip, A=7-11% (from a pressurized air supply line, e.g., of an Oculase MD) and W=1-3% (from a pressurized water supply line, e.g., of an Oculase MD). To reduce bleeding after removal the laser can be used in defocused mode at a setting such as mentioned for soft tissue coagulation.

For lesions such as the chalazions or cysts the laser is used to prepare the incision to access the lesion. For example, a small chalazion can be removed via a small laser cut at the back of the eyelid or at the front of the eyelid depending upon the clinical situation. Laser settings for this incision can be P=0.5-1 W, pulse frequency 20 Hz, $E_{pulse}$=25-50 mJ/pulse, tip type=OT4, A=7-11% (from a pressurized air supply line, e.g., of an Oculase MD) and W=1-3% (from a pressurized water supply line, e.g., of an Oculase MD). The eyelid is everted so that the surgeon has access to the back surface of the eyelid, and a small cut (about 3 mm) is made just on top of the chalazion. The lump is then drained and pressure is applied for a few minutes to stop any oozing of blood that may occur because of the operation. The Er,Cr:YSGG laser may also be used to seal the bleeding vessels. There is no need for stitches, and since the cut is at the back of the eyelid the cosmetic result can be excellent. If the chalazion is large and pushes on the skin of the eyelid then it is usually removed via a small incision in front of the eyelid through the skin. Care must be taken to follow the direction of the natural folds, wrinkles and/or creases on the skin. The laser cut can be about 3 mm in length, and it can be performed just on top of the chalazion. After drainage of the lesion the open wound is closed with very fine stitches which provide good cosmetic results at five to seven days post-operatively. All tissue lesions are sent for routine histopathology to confirm the nature of the tissue growth.**

Incision, Excision and Coagulation of Sclera

Sclerotomy

The Er,Cr:YSGG Oculase MD laser system is indicated for scleral incision procedures because of the great clinical capabilities of this wavelength to cut and remove scleral tissue with precision and with minimal to no superficial thermal effects. Scleral incision or sclerotomy can be preformed during vitreous surgery to provide a path for access into the vitreous cavity. For this purpose a small incision through the sclera of about 1 mm in length is performed to accommodate instruments such as vitreous cutters, vitreous endo illuminators, vitreous forceps, picks, or scissors through the sclera into the vitreous cavity. The appropriate location for incision is at approximately 3.5 mm posterior to the limbus. For standard vitrectomies three incisions are performed to provide access at three locations through the sclera, such locations typically being the superior nasal quadrant, the superior temporal quadrant, and the inferior temporal quadrant.

The instruments inserted through the sclera at the superior nasal and temporal quadrants usually change while the inferior quadrant is only used to insert the infusion cannula. The incision of the sclera with the Er,Cr:YSGG laser can be accomplished with a 400 μm diameter OZ4 or OT4 tip in contact mode or at about 0.5 mm off the tissue surface. The tip can be positioned perpendicularly to the surface or at an angle of about 50-60 degrees to the surface. To cut through the sclera a slight pressure can be applied onto the site with the tip slowly moved along the path of the cut. Parameters for such a sclerotomy using an OT4 or OZ4 tip can be P=0.25-0.35 W, pulse frequency of 15 or 20 Hz, $E_{pulse}$=12.5-17.5 mJ/pulse at 20 Hz and $E_{pulse}$=17-23 mJ/pulse at 15 Hz, A=7% (from a pressurized air supply line, e.g., of an Oculase MD) and W=1-3% (from a pressurized water supply line, e.g., of an Oculase MD). Depending on the selected settings the incision may take one or more passes to get through the sclera and choroid. If bleeding occurs during the incision of the choroid, the water spray can be reduced, and with an OG6 (4 or 6 mm length) tip in a defocused mode, approximately 3 mm off the surface, each side of the cut can be scanned to induce surface coagulation and reduce bleeding. The power setting for this procedure can be at about 0.25 W at a pulse frequency of 15-20 Hz. To finish the incision, cutting through the sclera and choroid can be continued with reduced or no water spray. During cutting with water spray effective suction is necessary to remove excess fluid and maintain good visibility.

Partial Thickness Scleral Flap

Some clinical indications require a partial incision through the sclera to prepare a scleral flap. This procedure, called a partial thickness scleral flap and commonly performed with scalpels, is usually performed at midthickness through the sclera but sometimes deeper at about 70-90% in depth. Most scleral flaps are performed as part of a trabeculectomy procedure, and others are to cover an exposed suture that resulted from an IOL or capsular expansion ring sutured to the sclera. The flaps are usually started at the limbus where the base of the flap is positioned and continued posteriorly on the sclera. The flap may be performed in any quadrant; however, the most common locations are in the superior quadrants of the eye. Basic shapes for partial thickness scleral flaps vary from square or trapezoid or rectangular to triangular types. The usual size of such flaps is about 2 mm×3 mm×2 mm for rectangular, 3 mm×3 mm×3 mm for square and 3 mm×3 mm for triangular shape. The incisions can be longer, i.e., 4-5 mm depending on the surgeon's preference. All flaps are attached closely to the limbus.

Suitable Er,Cr:YSGG laser settings for performing a partial thickness flap can be P=0.15-0.20 W, pulse frequency of 20 Hz, $E_{pulse}$=8-10 mJ/pulse, tip type=OZ2 or OZ3, A=7% (from a pressurized air supply line, e.g., of an Oculase MD) and W=1-3% (from a pressurized water supply line, e.g., of an Oculase MD). The flap preparation can begin with an outline that will provide the initial depth and shape, using the OZ2 or OZ3 tip in slight contact mode at the above mentioned settings. The process can start at one side of the base, near the limbus, with the tip being moved slowly along the perimeter of the flap. At this power setting several layers of cells will be removed. To control the depth of the cut into the sclera, the user should carefully observe the effect of laser on tissue and if necessary stop to check the depth of the preparation at the beginning of the outline. For a more conservative approach the tip can be used in non-contact mode about 1 mm off the surface to reduce the depth of incision.

On average the thickness of the sclera varies from 1000 to 300 μm at its thinnest point (behind the insertion of the extraocular muscles). Calibration of the initial penetration of laser into sclera should be about 150 μm in depth. To achieve this result processing should begin at the lower power setting in defocused mode about 1 mm from the surface, with subsequent verifying through visual observation of the initial depth produced near the limbus where the sclera is at its thickest point. After preparation of the outline processing should proceed with the lifting of the flap, such as by lifting of one corner of the tissue with a forceps and with an OZ3 tip positioned underneath and parallel to the surface starting the flap separation. Using a side to side motion the separation of tissue can be completed with precision.

For flaps that require a deeper thickness of ~70-90% into the sclera the surgeon can watch for the color change to determine the limit of the cutting depth. The change in color goes from white to bluish, due to the color of the choroid underlining the sclera with deeper incision into the sclera causing a darker bluish color of visualized tissue. Effective suction and fluid evacuation is necessary during this procedure to ensure adequate visibility at the tissue site. Preparing the deep thickness flap can begin with a deeper outline by adding one or more passes at the settings presented before. Extreme caution has to be used not to perforate through tissue when advancing into the sclera at depths close to the choroid. The recommended technique is to defocus and advance slowly with the tip inclined at 30-40 degrees to the surface, instead of 70-90 degrees, when getting deeper into the sclera. To separate the flap the laser or scalpel can be used. Either means require extreme caution to preserve the integrity of the thin scleral tissue underneath the flap. With the laser use the same parameters and technique as before to slowly separate the flap at the level of the outlined depth.

Excision of Scleral and Trabecular Tissue

A partial thickness flap is sometimes followed by a small resection of sclera and trabecular mesh to help with fluid removal (trabeculectomy). The part sclera part trabecular mesh tissue removal is a procedure performed to excise a piece of tissue that is no larger than a 1 mm square or a 1 mm by 2 mm rectangle. The location of the resection is at the level of the limbus. The partial thickness flap prepared before will be used to cover this opening to prevent intra-ocular infections and to limit the egress of fluid in a more controlled fashion. The laser excision can be performed using the same parameters and techniques as for the scleral excision presented before.

Iridectomy

Sometimes a trabeculectomy procedure requires an additional surgical intervention to remove of a small piece of iris tissue. This procedure, known as an iridectomy, is performed at the same time as the flap and the scleral/trabecular excisions. The purpose of this procedure is to create a new communication path between the posterior and anterior chambers of the eye. To perform this procedure an OZ3 tip can be used at the following parameter settings: P=0.15-0.20 W, pulse frequency of 20 Hz, $E_{pulse}$=8-10 mJ/pulse, A=7% (from a pressurized air supply line, e.g., of an Oculase MD) and W=1-3% (from a pressurized water supply line, e.g., of an Oculase MD). To pull tissue away from the lens a forceps can be used to lift the tissue at the periphery of the iris. With the OZ3 tip aimed sideways, cut can be performed at the base of the lifted tissue. A small piece of the iris will be quickly removed with great precision. In the absence of a laser this procedure is typically performed with a pair of scissors.

Ocular Tissue Coagulation

Laser tissue coagulation may be applied any time to control bleeding at the site. For example, before a scleral tissue incision the Er,Cr:YSGG laser may be used to coagulate the superficial vessels at the incision site to prevent excessive bleeding. For this procedure an OG6 (4 or 6 mm length) tip cab be used at the following settings: P=0.25 W, pulse frequency of 20 Hz, defocused mode at 2-3 mm from the surface, no spray. With the tip in defocused mode at about 1-2 mm off the surface the bleeding surface can be quickly scanned.

Presets for Tissue Procedures

The Oculase MD has sixteen user programmable presets available to be stored in the system memory. If the treatment protocol requires adjustment of settings, the clinician has the option to start with one of the selected settings and adjust parameters to appropriate values for the procedure. Treatment should begin at the lowest power necessary to produce the desired effect, with clinical judgment then being used to modify parameters in order to compensate for varying tissue type, composition, density and thickness specific to individual patients. If a particular new combination of customized values is especially effective and useful, the user can then store these values in the system as a new Preset. Changes to presets can be made and saved, according to each user's clinical judgment whereby appropriate adjustments are commensurately accorded to and for customization of the system. Before starting a new procedure indicated for this device in one's practice, work should be performed on tissue models to develop the technique and settings appropriate to the user. An example on calculating emitted power for a tip, such as the OT4 tip, includes a calibration factor of 0.90, a display power of 2 W, and an emitted power of 2 W×0.90=1.80 W. An example showing calculation of emitted power for a OZ2 tip includes a calibration factor of 0.30, a display power of 1 W, and an emitted power of 1 W×0.30=0.30 W.

According to modified embodiments, groupings of tissue treatments may be disposed around cuts (e.g., kerfs) to the sclera implemented in accordance with other technologies. In other modified embodiments, as an alternative or addition to any of the embodiments described herein, tissue treatments may be arranged to approximate or resemble prior-art surgical-formation shapes. For instance, tissue treatments may be applied to resemble, or in combination with, correctional patterns as described in U.S. Pat. No. 6,263,879, the contents of which are expressly incorporated herein by reference. In implementations wherein tissue treatments of the present invention are applied in combination with one or more of the patterns or ablation patterns disclosed in the aforementioned patent, the tissue treatments can be disposed for example along part or all of the boundary(ies) of the linear ablation pattern(s) with or without the ablation pattern(s) being formed as well. In modified embodiments, any of the above tissue treatments may be applied in combination with any other eye treatments to the extent compatible, or modifiable to be compatible, by one skilled in the art, with the present tissue treatments. For instance, the presently-described alterations (e.g., rotations and/or shifts) to the conjunctiva in connection with the formation of tissue treatments in the sclera may be modified and/or combined with other technologies (e.g., such as described in the aforementioned patent) involving applications or formations of treatments (e.g., ablations) to the sclera.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, it is intended that the present invention not be limited by the disclosed embodiments, but be defined by reference to the appended additional disclosure in claims format.

What is claimed is:

1. A method for treating an eye in need of one or more of a physiological and a vision correction, comprising;
   directing treatment energy onto an anatomic structure, wherein the treatment energy has a power of about 0.15-0.20 W, a pulse frequency of about 20 Hz, an $E_{pulse}$ of about 8-10 mJ/pulse, an air output from a pressurized air supply line, and a water output from a pressurized water supply line, wherein the treatment energy profile has one or more of a conical and a "V" shape; and
   wherein a characteristic or measurable parameter of the treatment energy drops by about 1 to about 20 percent for each 1 percent drop in depth within the anatomic structure.

2. The method as set forth in claim 1, wherein the treatment energy has a focal point, which is on or in the anatomic structure.

3. The method as set forth in claim 1, wherein the treatment energy comprises a beam of electromagnetic energy.

4. The method as set forth in claim 1, wherein the treatment energy is a beam of laser light.

5. The method as set forth in claim 1, wherein the anatomic structure is located beneath tissue above the anatomic structure, and wherein the anatomic structure, but not the tissue above the anatomic structure, is ablated.

6. The method as set forth in claim 1, wherein the anatomic structure is a sclera.

7. The method as set forth in claim 1, wherein the treatment energy is directed through a tip prior to being directed onto the anatomic structure.

8. The method as set forth in claim 1, wherein:
   the treatment energy passes through a tip prior to being directed onto the anatomic structure; and
   the tip is held in a non-contact mode to cut or ablate the anatomic structure.

9. The method as set forth in claim 8, wherein an initial penetration into the anatomic structure is performed with the tip about 1 mm from a surface of the anatomic structure.

10. The method as set forth in claim 8, wherein the holding of the tip in a non-contact mode is followed by contacting the anatomic structure with the tip to cut or ablate the anatomic structure.

11. The method as set forth in claim 1, wherein an initial penetration into the anatomic structure is performed in a non-contact, defocused mode followed by further penetration into the anatomic structure in a contact mode.

\* \* \* \* \*